US012715900B2

(12) United States Patent
Li et al.

(10) Patent No.: US 12,715,900 B2
(45) Date of Patent: Aug. 25, 2026

(54) PREPARATION METHOD FOR SEMAGLUTIDE

(71) Applicant: SHENZHEN JYMED TECHNOLOGY CO., LTD., Shenzhen (CN)

(72) Inventors: Xinyu Li, Shenzhen (CN); Yuqing Fu, Shenzhen (CN); Lixiang Zhang, Shenzhen (CN); Lin Yao, Shenzhen (CN); Wenjing Li, Shenzhen (CN)

(73) Assignee: Shenzhen Jymed Technology Co., LTD., Shenzhen (CN)

( * ) Notice: Subject to any disclaimer, the term of this patent is extended or adjusted under 35 U.S.C. 154(b) by 881 days.

(21) Appl. No.: 17/793,601

(22) PCT Filed: Jul. 9, 2020

(86) PCT No.: PCT/CN2020/101081
§ 371 (c)(1),
(2) Date: Jul. 18, 2022

(87) PCT Pub. No.: WO2021/143073
PCT Pub. Date: Jul. 22, 2021

(65) Prior Publication Data

US 2023/0133716 A1 May 4, 2023

(30) Foreign Application Priority Data

Jan. 19, 2020 (CN) ........................ 202010060888.3

(51) Int. Cl.
*C07K 14/605* (2006.01)

(52) U.S. Cl.
CPC ................................. *C07K 14/605* (2013.01)

(58) Field of Classification Search
None
See application file for complete search history.

(56) References Cited

U.S. PATENT DOCUMENTS

| | | | |
|---|---|---|---|
| 2015/0315260 | A1 | 11/2015 | Bossart et al. |
| 2018/0057558 | A1 | 3/2018 | Penias Navon et al. |
| 2019/0211073 | A1 | 7/2019 | Fu et al. |

FOREIGN PATENT DOCUMENTS

| | | | |
|---|---|---|---|
| CN | 104356224 | A | 2/2015 |
| CN | 105732798 | A | 7/2016 |
| CN | 106749613 | A | 5/2017 |
| CN | 107056927 | A | 8/2017 |
| CN | 107903317 | A | 4/2018 |
| CN | 108034004 | A | 5/2018 |
| CN | 108359006 | A | 8/2018 |
| CN | 105732798 | B | 10/2018 |
| CN | 109180801 | A | 1/2019 |
| CN | 109369798 | A | 2/2019 |
| CN | 109456401 | A | 3/2019 |
| CN | 109627317 | A | 4/2019 |
| CN | 110028573 | A | 7/2019 |
| CN | 110078816 | A | 8/2019 |
| CN | 110372785 | A | 10/2019 |
| CN | 110615836 | A | 12/2019 |
| WO | 2018032521 | A1 | 2/2018 |
| WO | 2018032843 | A1 | 2/2018 |
| WO | 2019069274 | A1 | 4/2019 |

OTHER PUBLICATIONS

Machine Translation of WO 2018032843, published Feb. 22, 2018. (Year: 2018).*

International Search Report and Written Opinion, and English Translation of the Search Report thereof, for International Application No. PCT/CN2020/101081, mailed Oct. 23, 2020 (13 pages).

Chinese Office Action for Chinese Counterpart Application No. 202080002993.X, mailed Aug. 30, 2022, (8 pages).

International Search Report and English Translation for International Application No. PCT/CN2020/114185, mailed Dec. 11, 2020, 6 pages.

First Chinese Office Action for Chinese Application No. 202010659555.2, mailed Aug. 31, 2022, 15 pages.

* cited by examiner

*Primary Examiner* — Noble E Jarrell
(74) *Attorney, Agent, or Firm* — Kagan Binder, PLLC

(57) ABSTRACT

A preparation method for semaglutide. The method comprises: producing a semaglutide resin by means of a solid-phase synthesis, producing crude semaglutide by cleavage and deprotection, producing refined semaglutide by purification and freeze-drying, comprising the solid-phase synthesis of a semaglutide 1-6 peptide fragment resin, which is cleaved and purified to serve as a first peptide fragment; and synthesizing a lysine having a sidechain group at locus 20 of semaglutide to serve as a second peptide fragment. In the method, prepared is a semaglutide loci 1-6 fully protected peptide fragment, which serves as a key starting material applied in the solid-phase synthesis of semaglutide, thus reducing the generation of D-His, D-Glu, D-Thr, D-Phe racemic impurities and +Gly impurities, reducing the difficulty of coarse product purification, increasing the purity and yield of semaglutide, reducing synthesis costs, and favoring industrialized large-scale production.

14 Claims, 1 Drawing Sheet

PREPARATION METHOD FOR SEMAGLUTIDE

TECHNICAL FIELD

The present disclosure relates to the field of polypeptide synthesis, in particular to a method for preparing semaglutide.

BACKGROUND

Glucagon-like peptide-1 (GLP-1) is a peptide hormone secreted by human intestinal L cells, which can promote the secretion of insulin, inhibit the secretion of glucagon, and have the effect of reducing blood glucose concentration, thus is used for the treatment of type II diabetes. However, native GLP-1 is unstable in vivo and is susceptible to rapid degradation by dipeptidyl peptidase-IV (DPP-IV).

Semaglutide, is a novel long-acting glucagon-like peptide-1 (GLP-1) analogue developed and produced by Novo Nordisk, Denmark, for the treatment of type II diabetes. Semaglutide has the effects of reducing blood glucose, losing weight, and protecting cardiovascular, and was approved by the FDA in December 2017. After the Lys side chain of semaglutide is modified by PEG, Glu, and octadecanedicarboxylic acid, the hydrophilicity is greatly improved, and the binding force with albumin is enhanced. In addition, after the mutation of Ala at the position 2 of the N-terminal of semaglutide to Aib, inactivation caused by DPP-IV enzymolysis is effectively avoided, the half-life reaches 40 h, and patients only need to inject once every week. The semaglutide has a CAS number of 910463-68-2, a molecular formula of C187H291N45O59, a molecular weight of 4113.64 g/mol, and a peptide sequence of: H-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-Octadecanedioic acid )-Glu-Phe-Ile-Ala-Trp-Leu-Val-Arg-Gly-Arg-Gly-OH.

At present, the reported methods for preparing semaglutide are roughly divided into two categories. One is to take Lys containing side chains as a fragment to be directly linked to the main chain of semaglutide to complete the synthesis. Patent CN104356224A discloses a method for preparing semaglutide including linking a side chain to the ε-$NH_2$ of Lys by using a liquid-phase method, and then condensing amino acids on a resin in sequence. The other is to complete the coupling of the main chain and side chain of semaglutide respectively. Patent CN 201511027176 discloses stepwise synthesizing semaglutide linear peptide in solid phase, synthesizing the side chain modifying group, removing the protecting group of Lys, coupling the side chain modifying group, and finally obtaining the polypeptide product by cleavage. Since semaglutide has a long sequence and a high proportion of hydrophobic amino acids, it is easy to form folding when synthesized by stepwise condensation of amino acids, which leads to serious shrinkage of the resin and prolongs the reaction time, and then producing, among the crude peptide, a variety of impurities having a property very close to that of the product, such as a racemate impurity of [D-His], namely, H-D-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-Octadecanedioic acid)-Glu-Phe-Ile-Ala-Trp-Leu-Val-Arg-Gly-Arg-Gly-OH; +Gly impurity, namely, H-His-Aib-Glu-Gly-Gly-Thr-Phe-Thr-Ser-Asp-Val-Ser-Ser-Tyr-Leu-Glu-Gly-Gln-Ala-Ala-Lys(AEEA-AEEA-γ-Glu-Octadecanedioic)-Glu-Phe-Ile-Ala-Trp-Leu-Val-Arg-Gly-Arg-Gly-OH; D-Phe impurity, namely, H-His-Aib-Glu-Gly-Thr-D-Phe-Thr-Ser-Asp-Val-Ser-Ser-Tyr-Leu-Glu-Gly-Gln-Ala-Ala-Lys(Octadecanedioic acid-γ-Glu-PEG-PEG)-Glu-Phe-Ile-Ala-Trp-Leu-Val-Arg-Gly-Arg-Gly-OH. The racemate impurity of [D-His], +Gly impurity, D-Phe impurity, and semaglutide target peptide have similar physicochemical properties, greatly increasing the difficulty of separation and purification of the semaglutide product, resulting in a greatly reduced product yield. Therefore, there is an urgent need for a method for synthesizing semaglutide with high purity and yield and low synthesis cost.

SUMMARY

In order to solve the problems in the existing synthesis process of semaglutide that racemate impurity of D-His, +Gly impurity, and D-Phe impurity are difficult to control, the purity and yield are low, and industrial production is not facilitated, the present disclosure provides a method for preparing semaglutide using a combination of fragment and stepwise synthesis. This method can effectively reduce racemate impurity of D-His, +Gly impurity, and D-Phe impurity, improve the purity and yield of semaglutide, and is beneficial to the mass production of semaglutide.

In order to achieve the object of the present disclosure, the present disclosure provides the following technical solutions.

A method for preparing semaglutide includes: performing a solid-phase synthesis to obtain a semaglutide resin, cleaving and deprotecting the semaglutide resin to obtain a crude peptide of semaglutide, purifying, and lyophilizing to obtain a refined peptide of semaglutide, wherein a monomer $R_1$-His($R_2$)-Aib-Glu($OR_3$)-Gly-Thr($R_4$)-Phe-$R_5$ is used at positions 1~6 and has a formula of:

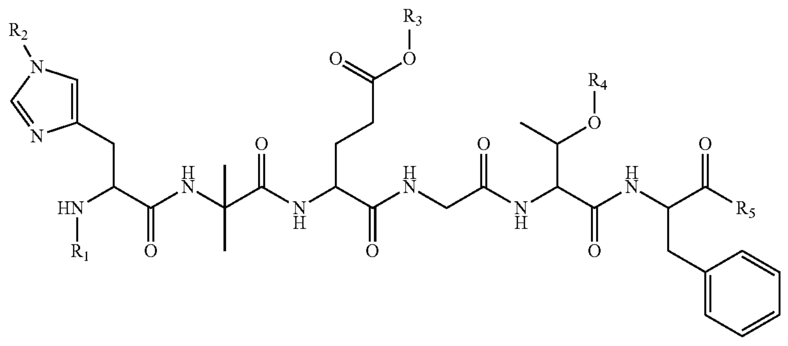

$R_1$ is hydrogen or an amino protecting group, $R_2$ is hydrogen or an amino protecting group, $R_3$ is an ester protecting group, $R_4$ is hydrogen or a hydroxyl protecting group, and $R_5$ is selected from the group consisting of OH, Cl, OBt, OSu, and OPfp.

Preferably, $R_1$ is selected from the group consisting of Fmoc, Ddc, Alloc, Boc, Trt, Dmb, Mmt, and Mtt.

Preferably, $R_2$ is selected from the group consisting of Fmoc, Boc, Trt, Dmb, Mmt, and Mtt.

Preferably, $R_3$ is selected from tBu or Bzl.

Preferably, $R_4$ is selected from tBu or Bzl.

Preferably, $R_5$ is selected from the group consisting of OH, OBt, OSu, and OPfp.

In some embodiments, $R_1$ is Boc, $R_2$ is Trt, $R_3$ is tBu, $R_4$ is tBu, and $R_5$ is OH.

Applicants have unexpectedly found that in the preparation of semaglutide, the synthesis of semaglutide using the monomer $R_1$-His($R_2$)-Aib-Glu($OR_3$)-Gly-Thr($R_4$)-Phe-$R_5$ at positions 1~6 can significantly inhibit/reduce the racemate impurity of [D-His], racemate impurity of [D-Glu], racemate impurity of [D-Thr], racemate impurity of [D-Phe], and +Gly impurity, obviously improving the yield and purity of the crude peptide of semaglutide.

Preferably, the method further includes that a monomer Fmoc-Lys(AEEA-AEEA-γ-Glu(OtBu)-Octadecanedioic acid mono-tert-butyl ester)-OH is used at position 20. Applicants have unexpectedly found that in the preparation of semaglutide, the use of the monomer Fmoc-Lys(AEEA-AEEA-γ-Glu(OtBu)-Octadecanedioic acid mono-tert-butyl ester)-OH at position 20 can enable the peptide intermediate to be easily inserted into SPPS, the remaining amino-terminal amino acids can be more easily coupled to the resin, and significantly inhibit/reduce the generation of mismatched peptide impurities (such as, amino acid deletion peptides, amino acid redundant peptides) and racemate peptide impurities, thus significantly improving the yield and purity of the crude peptide of somaglutide.

In some embodiments, a monomer Fmoc-Lys(AEEA-AEEA-γ-Glu(OtBu)-Octadecanedioic)-OH is used at position 20, and a monomer Boc-His(Trt)-Aib-Glu(OtBu)-N(Hmb)-Gly-Thr(tBu)-Phe-OH is used at positions 1~6.

Preferably, the $R_1$-His($R_2$)-Aib-Glu($OR_3$)-Gly-Thr($R_4$)-Phe-$R_5$ is coupled by a coupling system of DIC/HOBt, and the coupling system can be synergistically reduce the generation of the racemate impurity of D-Phe.

In some embodiments, the monomer $R_1$-His($R_2$)-Aib-Glu($OR_3$)-Gly-Thr($R_4$)-Phe-$R_5$ is obtained by coupling $R_1$-His($R_2$)-Aib-OH and a $R_6$-Glu($OR_3$)-Gly-Thr($R_4$)-Phe-resin, wherein $R_6$ is selected from the group consisting of Fmoc, Dde, Alloc, Boc, Trt, Dmb, Mmt, and Mtt. Preferably, the $R_6$-Glu($OR_3$)-Gly-Thr($R_4$)-Phe-resin is obtained by coupling $R_6$-Glu($OR_3$)-Gly-OH and a $R_7$-Thr($R_4$)-Phe-resin, wherein $R_7$ is selected from the group consisting of Fmoc, Dde, Alloc, Boc, Trt, Dmb, Mmt, and Mtt. By preparing the monomer $R_1$-His($R_2$)-Aib-Glu($OR_3$)-Gly-Thr($R_4$)-Phe-$R_5$ in this way, the content of D-Thr, D-Glu, and D-His impurities generated in the synthesis process can be further controlled.

In some embodiments, the monomer $R_1$-His($R_2$)-Aib-Glu($OR_3$)-Gly-Thr($R_4$)-Phe-$R_5$ is obtained by coupling $R_1$-His($R_2$)-Aib-Glu($OR_3$)-Gly-OH and a $R_7$-Thr($R_4$)-Phe-resin, wherein $R_7$ is selected from the group consisting of Fmoc, Dde, Alloc, Boc, Trt, Dmb, Mmt, and Mtt. More preferably, $R_1$-His($R_2$)-Aib-Glu($OR_3$)-Gly-OH is obtained by coupling $R_1$-His($R_2$)-Aib-OH and a $R_6$-Glu($OR_3$)-Gly-resin, wherein $R_6$ is selected from the group consisting of Fmoc, Dde, Alloc, Boc, Trt, Dmb, Mmt, and Mtt. By preparing the monomer $R_1$-His($R_2$)-Aib-Glu($OR_3$)-Gly-Thr($R_4$)-Phe-$R_5$ in this way, the content of D-Thr, D-Glu, and D-His impurities generated in the synthesis process can be further controlled.

In the present disclosure, a solid-phase synthesis method combining fragment and stepwise synthesis is adopted, wherein the 1-6 fully protected peptide fragment of semaglutide is prepared and used as the key starting material in the solid-phase synthesis of semaglutide, which greatly reducing the generation of D-His, D-Glu, D-Thr, D-Phe racemate impurities and +Gly impurity, significantly reducing the difficulty of crude product purification, greatly increasing the purity and yield of semaglutide, reducing synthesis costs, and facilitating industrialized large-scale production.

DETAILED DESCRIPTION OF THE EMBODIMENTS

Figure 1:
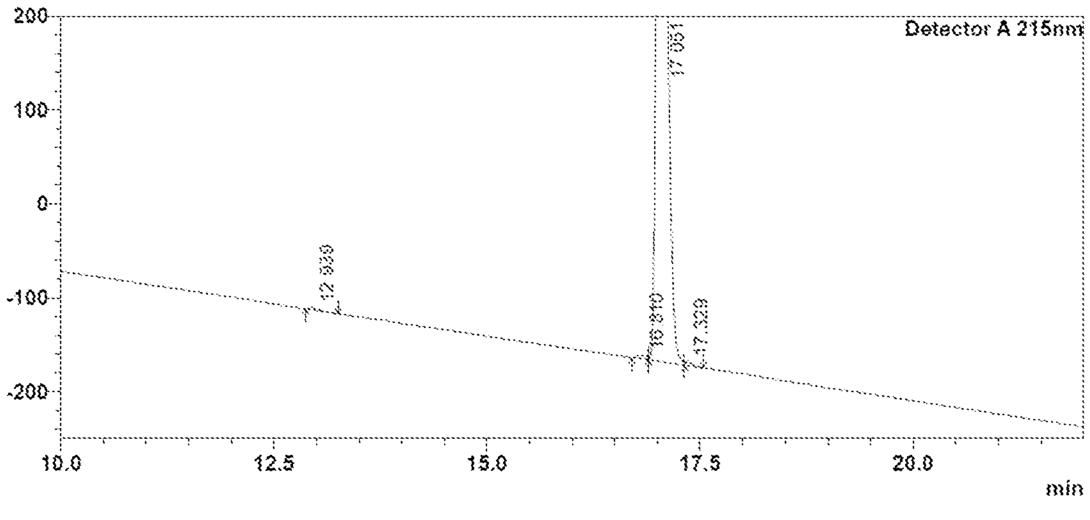
FIG. 1 shows an HPLC chromatogram of a peptide fragment of semaglutide at positions 1~6 synthesized in Example 7.

The above content of the present disclosure will be further described in detail below with reference to specific examples. However, it should not be construed as limiting the scope of the above-mentioned subject matter of the present disclosure to the following examples. All technologies implemented based on the above content of the present disclosure belong to the scope of the present disclosure.

The meanings of the abbreviations used in the present disclosure are listed in the following table:

| | |
|---|---|
| Fmoc | Fluorenylmethoxycarbonyl |
| Fmoc-AA | Fluorenylmethoxycarbonyl protected amino acid |
| TBTU | 2-(1H-benzotriazole L-1-yl)-1,1,3,3-tetramethyluronium tetrafluoroborate |
| HOBT | 1-Hydroxybenzotriazole |
| DIEA: | N,N-diisopropylethylamine |
| DIC: | N,N-diisopropylcarbodiimide |
| tBu | tert-butyl |
| BOC | tert-butoxycarbonyl |
| His | Histidine |
| Glu | Glutamate |
| Gly | Glycine |
| DMF | N,N-dmethylformamide |
| TFE | Trifluoroethanol |
| DCM | Dichloromethane |

Example 1 Preparation 1 of Boc-His(Trt)-Aib-Glu(OtBu)-Gly-Thr(tBlu)-Phe-OH

A. 150 g of 2-CTC resin with a degree of substitution of 1.10 mmol/g was added to a reactor, 500 ml of dichloromethane was added, and after mixing for 2 min, dichloromethane was filtered off. 500 ml of dichloromethane was added again, and after mixing for 40 min dichloromethane was filtered off. Finally, 500 ml of dichloromethane was added, and after mixing for 2 min dichloromethane was filtered off, and the resin was for later use.

B. 127.85 g of Fmoc-Phe-OH was weighed into a beaker, and 500 ml of DMF and 81.81 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 25 ml of methanol and 250 ml of DMF and a mixed solution of 40 ml of DIEA and 250 ml of DMF were added into the resin, and continued to mix and react for 1 h. After the reaction was completed, a suction filtration was performed, and the resin was washed for 5 times with 500 ml of DMF each time; then washed twice with 500 ml of methanol each time; and then washed twice with 500 ml of dichloromethane each time; finally washed for 3 times with 500 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 165.50 g of Fmoc-Phe-CTC resin was obtained, and the degree of substitution was detected to be 0.85 mmol/g.

D. All the Fmoc-Phe-CTC resin obtained in step C was poured into a reactor, swollen and mixed with 500 ml of DCM for 15 min, and then drained. 500 ml of piperidine/DMF solution with a volume concentration of 20% was added, mixed for 5 minutes at 20-30° C., and then drained. 500 ml of DMF was added, mixed for 5 minutes, and then drained. 500 ml of piperidine/DMF solution with a volume concentration of 20% was added, mixed for 10 minutes at 20-30° C., and then drained. 500 ml of DMF was added, mixed for 5 minutes, and then drained. The resin was washed repeatedly for 5 times with 500 ml of DMF for 5 minutes each time, and after the fourth washing, the filtrate was tested with a pH test paper, and the result showed that the pH was 6.5-7.0 which was qualified.

E. 111.83 g of Fmoc-Thr(tBu)-OH, 35.51 g of DIC, and 45.62 g of HOBT were weighed in turn into a clean 1 L of beaker, and 500 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 500 ml of DMF was added thereto, followed by mixing for 5 min and draining. The resin was washed repeatedly for 5 times with 500 ml of DMF for 5 minutes each time. The final test with ninhydrin was negative, that is, a Fmoc-Thr(tBu)-Phe-CTC resin was obtained.

F. According to the deprotection method of step D and the coupling method of step E described above, the amino acids Fmoc-Gly-OH, Fmoc-Glu(OtBu)-OH, Fmoc-Aib-OH, and Boc-His(Trt)-OH were coupled in sequence. The resin was washed for 5 times with 500 ml of dichloromethane each time; then washed twice with 500 ml of methanol each time; and then washed twice with 500 ml of dichloromethane each time; finally washed for 3 times with 500 ml of methanol each time, until the resin was fully dispersed. The resin was dried in a vacuum drying oven at 20-30° C. for 4 h to constant weight (weighed twice continuously, with an error of less than 1%). 295.65 g of fully protected Boc-His(Trt)-Aib-Glu(OtBu)-Gly-Thr(tBu)-Phe-CTC resin was obtained.

G. 20 g of the fully protected peptide resin of the CTC resin obtained in step F was added into 200 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 100 mL of DCM. The operation was repeated twice, and the filtrates were combined, then concentrated in vacuo until a volume of the filtrate was 30% of the original volume. Then the concentrated solution was slowly added to 1 L of the pre-cooled isobutyl ether, and centrifuged after sedimentation for 5 times with 200 mL of isobutyl ether each time, to obtain a white solid powder, which was first dried with nitrogen, then dried in a vacuum drying oven for 10 h, and then taken out and weighed to obtain 10.75 g of crude product of fully protected Boc-His(Trt)-Aib-Glu(OtBu)-Gly-Thr(tBu)-Phe-OH.

Example 2 Preparation of Fmoc-His(Boc)-Aib-Glu(OBzl)-Gly-Thr(tBu)-Phe-OBt

A. 100 g of 2-CTC resin with a degree of substitution of 1.10 mmol/g was added to a reactor, 500 ml of dichloromethane was added, and after mixing for 2 min, dichloromethane was filtered off. 500 ml of dichloromethane was added again, and after mixing for 40 min, dichloromethane was filtered off. Finally, 500 ml of dichloromethane was added, and after mixing for 2 min, dichloromethane was filtered off, and the resin was for later use.

B. 85.66 g of Fmoc-Phe-OH was weighed into a beaker, and 500 ml of DMF and 54.81 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 25 ml of methanol and 250 ml of DMF and a mixed solution of 27 ml of DIEA and 250 ml of DMF were added into the resin, and continued to mix and react for 1 h. After the reaction was completed, a suction filtration was performed, and the resin was washed for 5 times with 500 ml of DMF each time; then washed twice with 500 ml of methanol each time; and then washed twice with 500 ml of dichloromethane each time; finally washed for 3 times with 500 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 115.30 g of Fmoc-Phe-CTC resin was obtained, and the degree of substitution was detected to be 0.82 mmol/g.

D. All the Fmoc-Phe-CTC resin obtained in step C was poured into a reactor, swollen and mixed with 500 ml of DCM for 15 min, and then drained. 500 ml of piperidine/DMF solution with a volume concentration of 20% was added, mixed for 5 minutes at 20-30° C., and then drained. 500 ml of DMF was added, mixed for 5 minutes, and then drained. 500 ml of piperidine/DMF solution with a volume concentration of 20% was added, mixed for 10 minutes at 20-30° C., and then drained. 500 ml of DMF was added, mixed for 5 minutes, and then drained. The resin was washed repeatedly for 5 times with 500 ml of DMF for 5 minutes each time, and after the fourth washing, the filtrate was tested with a pH test paper, and the result showed that the pH was 6.5-7.0 which was qualified.

E. 75.16 g of Fmoc-Thr(tBu)-OH, 23.86 g of DIC, and 30.66 g of HOBT were weighed in turn into a clean 1 L of beaker, and 500 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 500 ml of DMF was added thereto, followed by mixing for 5 min and draining. The resin was washed repeatedly for 5 times with 500 ml of DMF for 5 minutes each time. The final test with ninhydrin was negative, that is, a Fmoc-Thr(tBu)-Phe-CTC resin was obtained.

F. According to the deprotection method of step D and the coupling method of step E described above, the amino acids Fmoc-Gly-OH, Fmoc-Glu(OBzl)-OH, Fmoc-Aib-OH, and Fmoc-His(Boc)-OH were coupled in sequence. The resin was washed for 5 times with 500 ml of dichloromethane each time; then washed twice with 500 ml of methanol each time; and then washed twice with 500 ml of dichloromethane each time; finally washed for 3 times with 500 ml of methanol each time, until the resin was fully dispersed. The resin was dried in a vacuum drying oven at 20-30° C. for 4 h to constant weight (weighed twice continuously, with an error of less than 1%). 204.25 g of fully protected Fmoc-His(Boc)-Aib-Glu(OBzl)-Gly-Thr(tBu)-Phe-CTC resin was obtained.

G. 20 g of the fully protected peptide resin of the CTC resin obtained in step F was added into 200 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 100 mL of DCM. The operation was repeated twice, and the filtrates were combined, then concentrated in vacuo until a volume of the filtrate was 30% of the original volume. Then the concentrated solution was slowly added to 1 L of the pre-cooled isobutyl ether, and centrifuged after sedimentation for 5 times with 200 mL of isobutyl ether each time, to obtain a white solid powder, which was first dried with nitrogen, then dried in a vacuum drying oven for 10 h, and then taken out and weighed to obtain 9.83 g of crude product of fully protected Fmoc-His(Boc)-Aib-Glu(OBzl)-Gly-Thr(tBu)-Phe-OH.

H. Fmoc-His(Boc)-Aib-Glu(OBzl)-Gly-Thr(tBu)-Phe-OH obtained in step G, 2.02 g of DIC, and 2.16 g of HOBT were dissolved in 50 ml of dichloromethane and the suspension was stirred for 1.5 hours at room temperature. After the reaction was completed, the precipitate was removed by filtration, and 10.46 g of Fmoc-His(Boc)-Aib-Glu(OBzl)-Gly-Thr(tBu)-Phe-OBt product was obtained after purification.

Example 3 Preparation of Fmoc-His(Trt)-Aib-Glu(OtBu)-Gly-Thr(tBu)-Phe-OSu

A. 120 g of 2-CTC resin with a degree of substitution of 1.10 mmol/g was added to a reactor, 500 ml of dichloromethane was added, and after mixing for 2 min, dichloromethane was filtered off. 500 ml of dichloromethane was added again, and after mixing for 40 min, dichloromethane was filtered off. Finally, 500 ml of dichloromethane was added, and after mixing for 2 min, dichloromethane was filtered off, and the resin was for later use.

B. 102.28 g of Fmoc-Phe-OH was weighed into a beaker, and 500 ml of DMF and 65.45 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 25 ml of methanol and 250 ml of DMF and a mixed solution of 32 ml of DIEA and 250 ml of DMF were added into the resin, and continued to mix and react for 1 h. After the reaction was completed, a suction filtration was performed, and the resin was washed for 5 times with 500 ml of DMF each time; then washed twice with 500 ml of methanol each time; and then washed twice with 500 ml of dichloromethane each time; finally washed for 3 times with 500 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 135.80 g of Fmoc-Phe-CTC resin was obtained, and the degree of substitution was detected to be 0.78 mmol/g.

D. All the Fmoc-Phe-CTC resin obtained in step C was poured into a reactor, swollen and mixed with 500 ml of DCM for 15 min, and then drained. 500 ml of piperidine/DMF solution with a volume concentration of 20% was added, mixed for 5 minutes at 20-30° C., and then drained. 500 ml of DMF was added, mixed for 5 minutes, and then drained. 500 ml of piperidine/DMF solution with a volume concentration of 20% was added, mixed for 10 minutes at 20-30° C., and then drained. 500 ml of DMF was added, mixed for 5 minutes, and then drained. The resin was washed repeatedly for 5 times with 500 ml of DMF for 5 minutes each time, and after the fourth washing, the filtrate was tested with a pH test paper, and the result showed that the pH was 6.5-7.0 which was qualified.

E. 84.20 g of Fmoc-Thr(tBu)-OH, 32.08 g of DIC, and 34.35 g of HOBT were weighed in turn into a clean 1 L of beaker, and 500 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 500 ml of DMF was added thereto, followed by mixing for 5 min and draining. The resin was washed repeatedly for 5 times with 500 ml of DMF for 5 minutes each time. The final test with ninhydrin was negative, that is, a Fmoc-Thr(tBu)-Phe-CTC resin was obtained.

F. According to the deprotection method of step D and the coupling method of step E described above, the amino acids Fmoc-Gly-OH, Fmoc-Glu(OtBu)-OH, Fmoc-Aib-OH, and Fmoc-His(Trt)-OH were coupled in sequence. The resin was washed for 5 times with 500 ml of dichloromethane each time; then washed twice with 500 ml of methanol each time; and then washed twice with 500 ml of dichloromethane each time; finally washed for 3 times with 500 ml of methanol each time, until the resin was fully dispersed. The resin was dried in a vacuum drying oven at 20-30° C. for 4 h to constant weight (weighed twice continuously, with an error of less than 1%). 241.36 g of fully protected Fmoc-His(Trt)-Aib-Glu(OtBu)-Gly-Thr(tBu)-Phe-CTC resin was obtained.

G. 20 g of the fully protected peptide resin of the CTC resin obtained in step F was added into 200 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 100 mL of DCM. The operation was repeated twice, and the filtrates were combined, then concentrated in vacuo until a volume of the filtrate was 30% of the original volume. Then the concentrated solution was slowly added to 1 L of the pre-cooled isobutyl ether, and centrifuged after sedimentation for 5 times with 200 mL of isobutyl ether each time, to obtain a white solid powder, which was first dried with nitrogen, then dried in a vacuum drying oven for 10 h, and then taken out and weighed to obtain 10.15 g of crude product of fully protected Fmoc-His(Trt)-Aib-Glu(OtBu)-Gly-Thr(tBu)-Phe-OH.

H. Fmoc-His(Trt)-Aib-Glu(OtBu)-Gly-Thr(tBu)-Phe-OH obtained in step G, 3.63 g of DCC, and 2.03 g of HOSu were dissolved in 50 ml of dichloromethane and the suspension was stirred for 1.5 hours at room temperature. After the reaction was completed, the precipitate was removed by filtration, and 10.94 g of Fmoc-His(Trt)-Aib-Glu(OtBu)-Gly-Thr(tBu)-Phe-OSu product was obtained after purification.

Example 4 Preparation of Boc-His(Trt)-Aib-OH

A. Preparation of Boc-His(Trt)-OH Active Ester

A 50 ml single-necked flask was placed in a low-temperature constant temperature stirring reactor, 2.91 g of Boc-His(Trt)-OH and 15 ml of DCM solvent were added, and then 1.10 g of pentafluorophenol was added. After stirring to dissolve until clear at 0° C., a solution of 1.34 g of DCC dissolved in 5 ml of DCM was added dropwise. After dropwise addition for 10 min, the temperature was raised to 25° C. for reaction for 3 h. The reaction was monitored by TLC (petroleum ether:ethyl acetate=1:1, 2 additional drops of acetic acid were added). After the reaction was completed, a suction filtration was performed, 5 ml of DCM was added for washing, and the filtrates were combined, and the solvent was removed by rotary evaporation to obtain 3.87 g of viscous material.

B. Preparation of Boc-His(Trt)-Aib-OH

A 25 ml single-necked flask was placed in a low-temperature constant temperature stirring reactor, 0.52 g of H-Aib-OH, 6 mL of 0.087 g/ml aqueous sodium carbonate solution, and 12 ml of $THF/H_2O$ (v/v=1:1) mixed solution were added, and the temperature was lowered to 0° C. 1.96 g of Boc-His(Trt)-OH active ester obtained in step A was weighed and dissolved in 6 ml of THF, and added dropwise to the single-necked flask. After dropwise addition for 5 min, the temperature was raised to 25° C. for reaction for 4 h. The reaction was monitored by TLC (petroleum ether:ethyl acetate=1:1, 2 additional drops of acetic acid were added). After the reaction was completed, an aqueous citric acid solution was added to adjust pH=5, and the mixture was extracted twice with 20 ml of ethyl acetate solvent each time. The organic phase was collected and washed twice with 20 ml of aqueous citric acid solution each time, then washed once with 20 ml of saturated brine, dried over anhydrous sodium sulfate, and the solvent was removed by rotary evaporation to obtain a viscous solid. 4 ml of petroleum ether/isopropyl ether (v/v=1:1) mixed solvent was added thereto, and slurried for 30 min, then suction-filtrated to obtain 1.31 g of viscous material in yellow.

Example 5 Preparation of Fmoc-Glu(OtBu)-Gly-OH

A. Preparation of Fmoc-Glu(OtBu)-OH Active Ester

A 50 ml single-necked flask was placed in a low-temperature constant temperature stirring reactor, 2.13 g of Fmoc-Glu(OtBu)-OH and 15 ml of DCM solvent were added, and then 1.10 g of pentafluorophenol was added. After stirring to dissolve until clear 0° C., a solution of 1.34 g of DCC dissolved in 5 ml of DCM was added dropwise. After dropwise addition for 10 min, the temperature was raised to 25° C. for reaction for 3 h. The reaction was monitored by TLC (petroleum ether:ethyl acetate=1:1, 2 additional drops of acetic acid were added). After the reaction was completed, a suction filtration was performed, 5 ml of DCM was added for washing, and the filtrates were combined, and the solvent was removed by rotary evaporation to obtain 2.84 g of viscous material.

B. Preparation of Fmoc-Glu(OtBu)-Gly-OH

A25 ml single-necked flask was placed in a low-temperature constant temperature stirring reactor, 0.45 g of H-Gly-OH, 6 mL of 0.087 g/ml aqueous sodium carbonate solution, and 12 ml of $THF/H_2O$ (v/v=1:1) mixed solution were added, and the temperature was lowered to 0° C. 1.42 g of Fmoc-Glu(OtBu)-OH active ester obtained in step A was weighed and dissolved in 6 ml of THF, and added dropwise to the single-necked flask. After dropwise addition for 5 min, the temperature was raised to 25° C. for reaction for 4 h. The reaction was monitored by TLC (petroleum ether:ethyl acetate=1:1, 2 additional drops of acetic acid were added). After the reaction was completed, an aqueous citric acid solution was added to adjust pH=5, and the mixture was extracted twice with 20 ml of ethyl acetate solvent each time. The organic phase was collected and washed twice with 20 ml of aqueous citric acid solution each time, then washed once with 20 ml of saturated brine, dried over anhydrous sodium sulfate, and the solvent was removed by rotary evaporation to obtain a viscous solid. 4 ml of petroleum ether/isopropyl ether (v/v=1:1) mixed solvent was added thereto, and slurried for 30 min, then suction-filtrated to obtain 1.06 g of viscous material in yellow.

Example 6 Preparation of Fmoc-Thr(tBu)-Phe-OH

A. Preparation of Fmoc-Thr(tBu)-OH Active Ester

A 50 ml single-necked flask was placed in a low-temperature constant temperature stirring reactor, 1.99 g of Fmoc-Thr(tBu)-OH and 15 ml of DCM solvent were added, and then 1.10 g of pentafluorophenol was added. After stirring to dissolve until clear at 0° C., a solution of 1.34 g of DCC dissolved in 5 ml of DCM was added dropwise. After dropwise addition for 10 min, the temperature was raised to 25° C. for reaction for 3 h. The reaction was monitored by TLC (petroleum ether:ethyl acetate=1:1, 2 additional drops of acetic acid were added). After the reaction was completed, a suction filtration was performed, 5 ml of DCM was added for washing, and the filtrates were combined, and the solvent was removed by rotary evaporation to obtain 2.70 g of viscous material.

B. Preparation of Fmoc-Thr(tBu)-Phe-OH

A25 ml single-necked flask was placed in a low-temperature constant temperature stirring reactor, 0.76 g of H-Phe-OH, 6 mL of 0.087 g/ml aqueous sodium carbonate solution, and 12 ml of THF/$H_2O$ (v/v=1:1) mixed solution were added, and the temperature was lowered to 0° C. 1.36 g of Fmoc-Thr(tBu)-OH active ester obtained in step A was weighed and dissolved in 6 ml of THF, and added dropwise to the single-necked flask. After dropwise addition for 5 min, the temperature was raised to 25° C. for reaction for 4 h. The reaction was monitored by TLC (petroleum ether:ethyl acetate=1:1, 2 additional drops of acetic acid were added). After the reaction was completed, an aqueous citric acid solution was added to adjust pH=5, and the mixture was extracted twice with 20 ml of ethyl acetate solvent each time. The organic phase was collected and washed twice with 20 ml of aqueous citric acid solution each time, then washed once with 20 ml of saturated brine, dried over anhydrous sodium sulfate, and the solvent was removed by rotary evaporation to obtain a viscous solid. 4 ml of petroleum ether/isopropyl ether (v/v=1:1) mixed solvent was added thereto, and slurried for 30 min, then suction-filtrated to obtain 1.15 g of viscous material in yellow.

Example 7 Preparation 2 of Boc-His(Trt)-Aib-Glu(OtBu)-Gly-Thr(tBu)-Phe-OH

A. 10 g of 2-CTC resin with a degree of substitution of 1.10 mmol/g was added to a reactor, 50 ml of dichloromethane was added, and after mixing for 2 min, dichloromethane was filtered off. 50 ml of dichloromethane was added again, and after mixing for 40 min, dichloromethane was filtered off. Finally, 50 ml of dichloromethane was added, and after mixing for 2 min, dichloromethane was filtered off, and the resin was for later use.

B. 11.98 g of Fmoc-Thr(tBu)-Phe-OH was weighed into a beaker, and 50 ml of DMF and 5.46 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 5 ml of methanol and 25 ml of DMF and a mixed solution of 3 ml of DIEA and 25 ml of DMF were added into the resin, and continued to mix and react for 1 h. After the reaction was completed, a suction filtration was performed, and the resin was washed for 5 times with 50 ml of DMF each time; then washed twice with 50 ml of methanol each time; and then washed twice with 50 ml of dichloromethane each time; finally washed for 3 times with 50 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 11.35 g of Fmoc-Thr(tBu)-Phe-CTC resin was obtained, and the degree of substitution was detected to be 0.83 mmol/g.

D. All the Fmoc-Thr(tBu)-Phe-CTC resin obtained in step C was poured into a reactor, swollen and mixed with 50 ml of DCM for 15 min, and then drained. 50 ml of piperidine/DMF solution with a volume concentration of 20% was added, mixed for 5 minutes at 20-30° C., and then drained. 50 ml of DMF was added, mixed for 5 minutes, and then drained. 50 ml of piperidine/DMF solution with a volume concentration of 20% was added, mixed for 10 minutes at 20-30° C., and then drained. 500 ml of DMF was added, mixed for 5 minutes, and then drained. The resin was washed repeatedly for 5 times with 50 ml of DMF for 5 minutes each time, and after the fourth washing, the filtrate was tested with a pH test paper, and the result showed that the pH was 6.5-7.0 which was qualified.

E. 9.09 g of Fmoc-Glu(OtBu)-Gly-OH, 2.85 g of DIC, and 3.06 g of HOBT were weighed in turn into a clean 1 L of beaker, and 50 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 50 ml of DMF was added thereto, followed by mixing for 5 min and draining. The resin was washed repeatedly for 5 times with 50 ml of DMF for 5 minutes each time. The final test with ninhydrin was negative, that is, a Fmoc-Glu(OtBu)-Gly-Thr(tBu)-Phe-CTC resin was obtained. The resin was washed for 5 times with 50 ml of dichloromethane each time; then washed twice with 50 ml of methanol each time; and then washed twice with 50 ml of dichloromethane each time; finally washed for 3 times with 50 ml of methanol each time, until the resin was fully dispersed. The resin was dried in a vacuum drying oven at 20-30° C. for 4 h to constant weight (weighed twice continuously, with an error of less than 1%). 17.15 g of fully protected Fmoc-Glu(OtBu)-Gly-Thr(tBu)-Phe-OH resin was obtained.

F. The Boc-His(Trt)-Aib-OH was coupled according to the deprotection method of step D and the coupling method of step E described above. The resin was washed for 5 times with 50 ml of dichloromethane each time; then washed twice with 50 ml of methanol each time; and then washed twice with 50 ml of dichloromethane each time; finally washed for 3 times with 50 ml of methanol each time, until the resin was fully dispersed. The resin was dried in a vacuum drying oven at 20-30° C. for 4 h to constant weight (weighed twice continuously, with an error of less than 1%). 20.65 g of fully protected Boc-His(Trt)-Aib-Glu(OtBu)-Gly-Thr(tBu)-Phe-CTC resin was obtained.

G. 10.00 g of the fully protected peptide resin of the CTC resin obtained in step F was added into 100 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 100 mL of DCM. The operation was repeated twice, and the filtrates were combined, then concentrated in vacuo until a volume of the filtrate was 30% of the original volume. Then the concentrated solution was slowly added to 200 mL of the pre-cooled isobutyl ether, and centrifuged after sedimentation for 5 times with 100 mL of isobutyl ether each time, to obtain a white solid powder, which was first dried with nitrogen, then dried in a vacuum drying oven for 10 h, and then taken out and weighed to obtain 9.86 g of crude product of fully protected Boc-His(Trt)-Aib-Glu (OtBu)-Gly-Thr(tBu)-Phe-OH, of which the HPLC chromatogram was shown in FIG. 1.

Example 8 Preparation of Fmoc-His(Trt)-Aib-OH

A. Preparation of Fmoc-His(Trt)-OH Active Ester

A 50 ml single-necked flask was placed in a low-temperature constant temperature stirring reactor, 2.39 g of Fmoc-His(Trt)-OH and 15 ml of DCM solvent were added, and then 1.10 g of pentafluorophenol was added. After stirring to dissolve until clear at 0° C., a solution of 1.34 g of DCC dissolved in 5 ml of DCM was added dropwise. After dropwise addition for 10 min, the temperature was raised to 25° C. for reaction for 3 h. The reaction was monitored by TLC (petroleum ether:ethyl acetate=1:1, 2 additional drops of acetic acid were added). After the reaction was completed, a suction filtration was performed, 5 ml of DCM was added for washing, and the filtrates were combined, and the solvent was removed by rotary evaporation to obtain 3.06 g of viscous material.

B. Preparation of Fmoc-His(Trt)-Aib-OH

A25 ml single-necked flask was placed in a low-temperature constant temperature stirring reactor, 0.76 g of H-Aib-OH, 6 mL of 0.087 g/ml aqueous sodium carbonate solution, and 12 ml of THF/$H_2O$ (v/v=1:1) mixed solution were added, and the temperature was lowered to 0° C. 1.52 g of Fmoc-His(Trt)-OH active ester obtained in step A was weighed and dissolved in 6 ml of THF, and added dropwise to the single-necked flask. After dropwise addition for 5 min, the temperature was raised to 25° C. for reaction for 4 h. The reaction was monitored by TLC (petroleum ether:ethyl acetate=1:1, 2 additional drops of acetic acid were added). After the reaction was completed, an aqueous citric acid solution was added to adjust pH=5, and the mixture was extracted twice with 20 ml of ethyl acetate solvent each time. The organic phase was collected and washed twice with 20 ml of aqueous citric acid solution each time, then washed once with 20 ml of saturated brine, dried over anhydrous sodium sulfate, and the solvent was removed by rotary evaporation to obtain a viscous solid. 4 ml of petroleum ether/isopropyl ether (v/v=1:1) mixed solvent was added thereto, and slurried for 30 min, then suction-filtrated to obtain 1.21 g of viscous material in yellow.

Example 9 Preparation of Fmoc-His(Trt)-Aib-Glu(OBzl)-Gly-OH

A. 20 g of 2-CTC resin with a degree of substitution of 1.10 mmol/g was added to a reactor, 100 ml of dichloromethane was added, and after mixing for 2 min, dichloromethane was filtered off. 100 ml of dichloromethane was added again, and after mixing for 40 min, dichloromethane was filtered off. Finally, 100 ml of dichloromethane was added, and after mixing for 2 min, dichloromethane was filtered off, and the resin was for later use.

B. 13.08 g of Fmoc-Gly-OH was weighed into a beaker, and 100 ml of DMF and 10.92 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 10 ml of methanol and 50 ml of DMF and a mixed solution of 5 ml of DIEA and 50 ml of DMF were added into the resin, and continued to mix and react for 1 h. After the reaction was completed, a suction filtration was performed, and the resin was washed for 5 times with 100 ml of DMF each time; then washed twice with 100 ml of methanol each time; and then washed twice with 100 ml of dichloromethane each time; finally washed for 3 times with 100 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 22.77 g of Fmoc-Gly-CTC resin was obtained, and the degree of substitution was detected to be 0.86 mmol/g.

D. All the Fmoc-Gly-CTC resin obtained in step C was poured into a reactor, swollen and mixed with 100 ml of DCM for 15 min, and then drained. 100 ml of piperidine/DMF solution with a volume concentration of 20% was added, mixed for 5 minutes at 20-30° C., and then drained. 100 ml of DMF was added, mixed for 5 minutes, and then drained. 100 ml of piperidine/DMF solution with a volume concentration of 20% was added, mixed for 10 minutes at 20-30° C., and then drained. 100 ml of DMF was added, mixed for 5 minutes, and then drained. The resin was washed repeatedly for 5 times with 100 ml of DMF for 5 minutes each time, and after the fourth washing, the filtrate was tested with a pH test paper, and the result showed that the pH was 6.5-7.0 which was qualified.

E. 18.38 g of Fmoc-Glu(OBzl)-OH, 6.06 g of DIC, and 8.10 g of HOBT were weighed in turn into a clean 1 L of beaker, and 100 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 50 ml of DMF was added thereto, followed by mixing for 5 min and draining. The resin was washed repeatedly for 5 times with 100 ml of DMF for 5 minutes each time. The final test with ninhydrin was negative, that is, a Fmoc-Glu(OBzl)-Gly-CTC resin was obtained.

F. The Fmoc-His(Trt)-Aib-OH obtained in Example 8 was coupled according to the deprotection method of step D and the coupling method of step E described above. The resin was washed for 5 times with 100 ml of dichloromethane each time; then washed twice with 50 ml of methanol each time; and then washed twice with 100 ml of dichloromethane each time; finally washed for 3 times with 100 ml of methanol each time, until the resin was fully dispersed. The resin was dried in a vacuum drying oven at 20-30° C. for 4 h to constant weight (weighed twice continuously, with an error of less than 1%). 36.85 g of fully protected Fmoc-His (Trt)-Aib-Glu(OBzl)-Gly-CTC resin was obtained.

G. 20.00 g of the fully protected peptide resin of the CTC resin obtained in step F was added into 200 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 200 mL of DCM. The operation was repeated twice, and the filtrates were combined, then concentrated in vacuo until a volume of the filtrate was 30% of the original volume. Then the concentrated solution was slowly added to 400 mL of the pre-cooled isobutyl ether, and centrifuged after sedimentation for 5 times with 200 mL of isobutyl ether each time, to obtain a white solid powder, which was first dried with nitrogen, then dried in a vacuum drying oven for 10 h, and then taken out and weighed to obtain 10.52 g of crude product of fully protected Fmoc-His(Trt)-Aib-Glu(OBzl)-Gly-OH.

Example 10 Preparation of Fmoc-His(Trt)-Aib-Glu(OBzl)-Gly-Thr(tBu)-Phe-OH

A. 5.00 g of 2-CTC resin with a degree of substitution of 1.10 mmol/g was added to a reactor, 25 ml of dichloromethane was added, and after mixing for 2 min, dichloromethane was filtered off. 25 ml of dichloromethane was added again, and after mixing for 40 min, dichloromethane was filtered off. Finally, 25 ml of dichloromethane was added, and after mixing for 2 min, dichloromethane was filtered off, and the resin was for later use.

B. 5.99 g of Fmoc-Thr(tBu)-Phe-OH was weighed into a beaker, and 50 ml of DMF and 2.73 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 5 ml of methanol and 25 ml of DMF and a mixed solution of 1.5 ml of DIEA and 25 ml of DMF were added into the resin, and continued to mix and react for 1 h. After the reaction was completed, a suction filtration was performed, and the resin was washed for 5 times with 25 ml of DMF each time; then washed twice with 25 ml of methanol each time; and then washed twice with 25 ml of dichloromethane each time; finally washed for 3 times with 25 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 5.78 g of Fmoc-Thr(tBu)-Phe-CTC resin was obtained, and the degree of substitution was detected to be 0.81 mmol/g.

D. All the Fmoc-Thr(tBu)-Phe-CTC resin obtained in step C was poured into a reactor, swollen and mixed with 25 ml of DCM for 15 min, and then drained. 25 ml of piperidine/DMF solution with a volume concentration of 20% was added, mixed for 5 minutes at 20-30° C., and then drained. 25 ml of DMF was added, mixed for 5 minutes, and then drained. 25 ml of piperidine/DMF solution with a volume concentration of 20% was added, mixed for 10 minutes at 20-30° C., and then drained. 25 ml of DMF was added, mixed for 5 minutes, and then drained. The resin was washed repeatedly for 5 times with 25 ml of DMF for 5 minutes each time, and after the fourth washing, the filtrate was tested with a pH test paper, and the result showed that the pH was 6.5-7.0 which was qualified.

E. 6.89 g of Fmoc-His(Trt)-Aib-Glu(OBzl)-Gly-OH obtained in Example 9, 1.06 g of DIC, and 1.14 g of HOBT were weighed in turn into a clean 1 L of beaker, and 50 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 25 ml of DMF was added thereto, followed by mixing for 5 min and draining. The resin was washed repeatedly for 5 times with 25 ml of DMF for 5 minutes each time. The final test with ninhydrin was negative, that is, a Fmoc-His(Trt)-Aib-Glu(OBzl)-Gly-Thr(tBu)-Phe-CTC resin was obtained. The resin was washed for 5 times with 25 ml of dichloromethane each time; then washed twice with 25 ml of methanol each time; and then washed twice with 25 ml of dichloromethane each time; finally washed for 3 times with 25 ml of methanol each time, until the resin was fully dispersed. The resin was dried in a vacuum drying oven at 20-30° C. for 4 h to constant weight (weighed twice continuously, with an error of less than 1%). 10.05 g of fully protected Fmoc-His(Trt)-Aib-Glu(OBzl)-Gly-Thr(tBu)-Phe-OH resin was obtained.

F. 10.05 g of the fully protected peptide resin of the CTC resin obtained in step E was added into 100 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 100 mL of DCM. The operation was repeated twice, and the filtrates were combined, then concentrated in vacuo until a volume of the filtrate was 30% of the original volume. Then the concentrated solution was slowly added to 200 mL of the pre-cooled isobutyl ether, and centrifuged after sedimentation for 5 times with 100 mL of isobutyl ether each time, to obtain a white solid powder, which was first dried with nitrogen, then dried in a vacuum drying oven for 10 h, and then taken out and weighed to obtain 5.12 g of crude product of fully protected Fmoc-His(Trt)-Aib-Glu(OBzl)-Gly-Thr(tBu)-Phe-OH.

Example 11 Boc-His(Trt)-Aib-Glu(OtBu)-Gly-Thr(tBu)-Phe-OH

A. 120 g of 2-CTC resin with a degree of substitution of 1.10 mmol/g was added to a reactor, 500 ml of dichloromethane was added, and after mixing for 2 min, dichloromethane was filtered off. 500 ml of dichloromethane was added again, and after mixing for 40 min, dichloromethane was filtered off. Finally, 500 ml of dichloromethane was added, and after mixing for 2 min, dichloromethane was filtered off, and the resin was for later use.

B. 102.28 g of Fmoc-Phe-OH was weighed into a beaker, and 500 ml of DMF and 65.45 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 25 ml of methanol and 250 ml of DMF and a mixed solution of 35 ml of DIEA and 250 ml of DMF were added into the resin, and continued to mix and react for 1 h. After the reaction was completed, a suction filtration was performed, and the resin was washed for 5 times with 500 ml of DMF each time; then washed twice with 500 ml of methanol each time; and then washed twice with 500 ml of dichloromethane each time; finally washed for 3 times with 500 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 142.54 g of Fmoc-Phe-CTC resin was obtained, and the degree of substitution was detected to be 0.83 mmol/g.

D. All the Fmoc-Phe-CTC resin obtained in step C was poured into a reactor, swollen and mixed with 500 ml of DCM for 15 min, and then drained. 500 ml of piperidine/DMF solution with a volume concentration of 20% was added, mixed for 5 minutes at 20-30° C., and then drained. 500 ml of DMF was added, mixed for 5 minutes, and then drained. 500 ml of piperidine/DMF solution with a volume concentration of 20% was added, mixed for 10 minutes at 20-30° C., and then drained. 500 ml of DMF was added, mixed for 5 minutes, and then drained. The resin was washed repeatedly for 5 times with 500 ml of DMF for 5 minutes each time, and after the fourth washing, the filtrate was tested with a pH test paper, and the result showed that the pH was 6.5-7.0 which was qualified.

E. 94.05 g of Fmoc-Thr(tBu)-OH, 29.86 g of DIC, and 38.37 g of HOBT were weighed in turn into a clean 1 L of beaker, and 500 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 500 ml of DMF was added thereto, followed by mixing for 5 min and draining. The resin was washed repeatedly for 5 times with 500 ml of DMF for 5 minutes each time. The final test with ninhydrin was negative, that is, a Fmoc-Thr(tBu)-Phe-CTC resin was obtained.

F. According to the deprotection method of step D and the coupling method of step E described above, the amino acids Fmoc-Gly-OH, Fmoc-Glu(OtBu)-OH, and Boc-His(Trt)-Aib-OH were coupled in sequence. The resin was washed for 5 times with 500 ml of dichloromethane each time; then washed twice with 500 ml of methanol each time; and then washed twice with 500 ml of dichloromethane each time; finally washed for 3 times with 500 ml of methanol each time, until the resin was fully dispersed. The resin was dried in a vacuum drying oven at 20-30° C. for 4 h to constant weight (weighed twice continuously, with an error of less than 1%). 237.58 g of fully protected Boc-His(Trt)-Aib-Glu (OtBu)-Gly-Thr(tBu)-Phe-CTC resin was obtained.

G. 50 g of the fully protected peptide resin of the CTC resin obtained in step F was added into 500 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 500 mL of DCM. The operation was repeated twice, and the filtrates were combined, then concentrated in vacuo until a volume of the filtrate was 30% of the original volume. Then the concentrated solution was slowly added to 2.5 L of the pre-cooled isobutyl ether, and centrifuged after sedimentation for 5 times with 500 mL of isobutyl ether each time, to obtain a white solid powder, which was first dried with nitrogen, then dried in a vacuum drying oven for 10 h, and then taken out and weighed to obtain 24.71 g of crude product of fully protected Boc-His(Trt)-Aib-Glu (OtBu)-Gly-Thr(tBu)-Phe-OH.

Example 12 Preparation of Fmoc-Lys(AEEA-AEEA-γ-Glu(OtBu)-Octadecanedioic acid mono-tert-butyl ester)-OH A. 150 g of 2-CTC resin with a degree of substitution of 1.05 mmol/g was added to a reactor, 500 ml of dichloromethane was added, and after mixing for 2 min, dichloromethane was filtered off. 500 ml of dichloromethane was added again, and after mixing for 40 min, dichloromethane was filtered off. Finally, 500 ml of dichloromethane was added, and after mixing for 2 min, dichloromethane was filtered off, and the resin was for later use.

B. 121.44 g of Fmoc-AEEA-OH was weighed into a beaker, and 500 ml of DMF and 76.18 ml of DIEA were added. The solution was stirred and activated at 0-10° C. for 5 minutes, then poured into the CTC resin obtained in step A, and then mixed and reacted for 4 h at 20-25° C. After the reaction was completed, DMF was filtered off. A mixed solution of 25 ml of methanol and 250 ml of DMF and a mixed solution of 40 ml of DIEA and 250 ml of DMF were added into the resin, and continued to mix and react for 1 h. After the reaction was completed, a suction filtration was performed, and the resin was washed for 5 times with 500 ml of DMF each time; then washed twice with 500 ml of methanol each time; and then washed twice with 500 ml of dichloromethane each time; finally washed for 3 times with 500 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 140.20 g of Fmoc-AEEA-CTC resin was obtained, and the degree of substitution was detected to be 0.73 mmol/g.

D. All the Fmoc-AEEA-CTC resin obtained in step C was poured into a reactor, swollen and mixed with 500 ml of DCM for 15 min, and then drained. 500 ml of piperidine/DMF solution with a volume concentration of 20% was added, mixed for 5 minutes at 20-30° C., and then drained. 500 ml of DMF was added, mixed for 5 minutes, and then drained. 500 ml of piperidine/DMF solution with a volume concentration of 20% was added, mixed for 10 minutes at 20-30° C., and then drained. 500 ml of DMF was added, mixed for 5 minutes, and then drained. The resin was washed repeatedly for 5 times with 500 ml of DMF for 5 minutes each time, and after the fourth washing, the filtrate was tested with a pH test paper, and the result showed that the pH was 6.5-7.0 which was qualified.

E. 108.07 g of Fmoc-AEEA-OH, 35.42 g of DIC, and 39.59 g of HOBT were weighed in turn into a clean 1 L of beaker, and 500 ml of DMF/DCM solution with a volume ratio of 1:1 was added. The beaker was placed in ice water, and the mixture was stirred and dissolved at 0-10° C. with a mechanical stirrer. After the temperature was constant, the temperature was maintained and the solution was stirred and activated for 5 min. The above activated solution was slowly added to a reactor, and mixed and reacted for 2 h at 20-25° C. After the reaction was completed, the reaction mixture was drained, and 500 ml of DMF was added thereto, followed by mixing for 5 min and draining. The resin was washed repeatedly for 5 times with 500 ml of DMF for 5 minutes each time. The final test with ninhydrin was negative, that is, a Fmoc-AEEA-AEEA-CTC resin was obtained.

F. According to the deprotection method of step D and the coupling method of step E described above, the amino acid Fmoc-Glu(OH)-OtBu and mono-tert-butyl octadecanedioate were coupled in sequence. The resin was washed for 5 times with 500 ml of dichloromethane each time; then washed twice with 500 ml of methanol each time; and then washed twice with 500 ml of dichloromethane each time; finally washed for 3 times with 500 ml of methanol each time, until the resin was fully dispersed. The resin was dried in a vacuum drying oven at 20-30° C. for 4 h to constant weight (weighed twice continuously, with an error of less than 1%). 255.40 g of Octadecanedioic acid mono-tert-butyl ester-γ-Glu(OtBu)-AEEA-AEEA-CTC resin was obtained.

G. 30 g of the fully protected peptide resin of the CTC resin obtained in step F was added into 300 mL of the lysis solution with a ratio of TFE:DCM=1:4 (volume ratio) at 15° C., and heated up to 30° C., continued to stir and react for 3 h. Then, the reaction mixture was filtered through a sand core funnel, and the filtered resin was washed with 100 mL of DCM. The operation was repeated twice, and the filtrates were combined, then concentrated in vacuo until a volume of the filtrate was 30% of the original volume. Then the concentrated solution was slowly added to 2 L of the pre-cooled isobutyl ether, and centrifuged after sedimentation for 5 times with 300 mL of isobutyl ether each time, to obtain a white solid powder, which was first dried with nitrogen, then dried in a vacuum drying oven for 10 h, and then taken out and weighed to obtain 11.65 g of crude product of Octadecanedioic acid mono-tert-butyl ester-γ-Glu(OtBu)-AEEA-AEEA-OH.

H. 5 g of crude product of Octadecanedioic acid mono-tert-butyl ester-γ-Glu(OtBu)-AEEA-AEEA-OH obtained in step G was dissolved in 10 mL of DCM, and 2.2 g of pentafluorophenol was added. 2.4 g of DCC was weighed and dissolved in 10 mL of DCM, the DCC solution was slowly added dropwise to the reaction solution, and stirred for reaction for 1.0 h. After completion of the reaction detected by TLC, a filtration was performed. The filtrate was washed with saturated brine once and with water once, then the DCM solution was dried over anhydrous sodium sulfate, concentrated to dryness, and then dissolved in an appropriate amount of acetonitrile. 6.08 g of Fmoc-Lys-OH.HCl was weighed and dissolved in acetonitrile/water (acetonitrile/water=1/2), 7.5 mL of DIEA was added, and stirred for 15 minutes. The above reaction solution was slowly added dropwise to the Fmoc-Lys-OH solution, and stirred and reacted for 1.5 h. Dilute hydrochloric acid was added to adjust the pH to about 6, and a small amount of DCM was added for extraction. After purification, 2.85 g of Fmoc-Lys(AEEA-AEEA-γ-Glu (OtBu)-Octadecanedioic acid mono-tert-butyl ester)-OH was obtained.

Example 13 Preparation of Fmoc-Gly-Wang Resin with a Degree of Substitution of 0.30 mmol/g A. 10 g of Wang resin with a degree of substitution of 0.9 mmol/g was added to a reactor, 100 ml of dichloromethane was added, and after mixing for 2 min, dichloromethane was filtered off. 100 ml of dichloromethane was added again, and after mixing for 40 min, dichloromethane was filtered off. Finally, 100 ml of dichloromethane was added, and after mixing for 2 min, dichloromethane was filtered off, and the resin was for later use.

B. 8.03 g of Fmoc-Gly-OH and 4.38 g of HOBT were weighed into a beaker, and 100 ml of DMF and 4.46 ml of DIEA were added. The solution was stirred and activated at 0-10° C. for 5 minutes, then poured into the Wang resin obtained in step A, 0.16 g of DMAP was added and then mixed for 4 h at 20-25° C. After the reaction was completed, 8.5 ml of acetic anhydride was added, and continued to mix for 1 h. After the reaction was completed, a suction filtration was performed, and the resin was washed for 5 times with 100 ml of DMF each time; then washed twice with 100 ml of methanol each time; and then washed twice with 100 ml of dichloromethane each time; finally washed for 3 times with 100 ml of methanol each time, until the resin was fully dispersed.

C. The resin obtained in step B was dried in a vacuum drying oven at 20-30° C. for 4 h to constant weight (weighed twice continuously, with an error of less than 1%). After drying, 13 g of Fmoc-Gly-Wang resin was obtained, and the degree of substitution was detected by UV to be 0.30 mmol/g.

Example 14 Preparation 1 of Crude Peptide of Semaglutide

A. 10 g of Fmoc-Gly-Wang resin obtained in Example 13 was poured into a reactor, swollen and mixed with 100 ml of DCM for 15 min, and then drained. 100 ml of piperidine/DMF solution with a volume concentration of 20% was added, mixed for 5 minutes at 20-30° C., and then drained. 100 ml of DMF was added, mixed for 5 minutes, and then drained. 100 ml of piperidine/DMF solution with a volume concentration of 20% was added, mixed for 10 minutes at 20-30° C., and then drained. 100 ml of DMF was added, mixed for 5 minutes, and then drained. The resin was washed repeatedly for 8 times with 100 ml of DMF for 5 minutes each time, and after the seventh washing, the filtrate was tested with a pH test paper, and the result showed that the pH was 6.5-7.0 which was qualified.

B. 3.89 g of Fmoc-Arg(Pbf)-OH, 1.16 g of TBTU, and 0.49 g of HOBT were weighed in turn into a clean 1 L of beaker, and 100 ml of DMF/DCM solution with a volume ratio of 1:1 was added. The beaker was placed in ice water, and the mixture was stirred and dissolved at 0-10° C. with a mechanical stirrer. After the temperature was constant, 0.50 mL of DIEA was added, the temperature was maintained and the solution was stirred and activated for 5 min. The above activated solution was slowly added to a reactor, and mixed for 2 h at 20-25° C. After the reaction was completed, the reaction mixture was drained, and 100 ml of DMF was added thereto, followed by mixing for 5 min and draining. The resin was washed repeatedly for 6 times with 100 ml of DMF for 5 minutes each time. The final test with ninhydrin was negative, that is, a Fmoc-Arg-Gly-Wang resin was obtained.

C. According to the deprotection method of step A and the coupling method of step B described above and based on the sequence of main chain amino acids, the remaining amino acids or peptide fragments were coupled in sequence, namely: coupling of Fmoc-Gly-OH, Fmoc-Arg (Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(AEEA-AEEA-γ-Glu(OtBu)-Octadecanedioic acid mono-tert-butyl ester)-OH obtained in Example 12, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr (tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, and Fmoc-His(Trt)-Aib-Glu (OBzl)-Gly-Thr(tBu)-Phe-OBt obtained in Example 2. Fmoc-Gly-OH, Fmoc-Arg (Pbf)-OH, and Fmoc-Val-OH were coupled by a coupling system of DIC/Cl-HOBt and a DMF solvent. Fmoc-Leu-OH, Fmoc-Trp (Boc)-OH, Fmoc-Ile-OH were coupled by a coupling system of TBTU/HOBt/DIEA and a DCM solvent. Fmoc-Glu(OtBu)-OH was coupled by a coupling system of TBTU/Cl-HOBt/DIEA. Fmoc-Phe-OH was coupled by a coupling system of TBTU/HOAt/DIEA. Fmoc-Ala-OH was coupled by a coupling system of TBTU/DIEA. Fmoc-Ser(tBu)-OH was coupled by a coupling system of PyBop/DIEA. Fmoc-Thr(tBu)-OH was coupled by a coupling system of PyAop/DIEA. Fmoc-Lys(AEEA-AEEA-γ-Glu(OtBu)-Octadecanedioic acid mono-tert-butyl ester)-OH was coupled by a coupling system of COMU/DIEA and a mixed solvent of NMP/DMSO=1:1. The resin was washed for 5 times with 100 ml of dichloromethane each time; then washed twice with 100 ml of methanol each time; and then washed twice with 100 ml of dichloromethane each time; finally washed for 3 times with 100 ml of methanol each time, until the resin was fully dispersed. The resin was dried in a vacuum drying oven at 20-30° C. for 4 h to constant weight (weighed twice continuously, with an error of less than 1%). 21.65 g of peptide resin of semaglutide was obtained.

Figure 2:
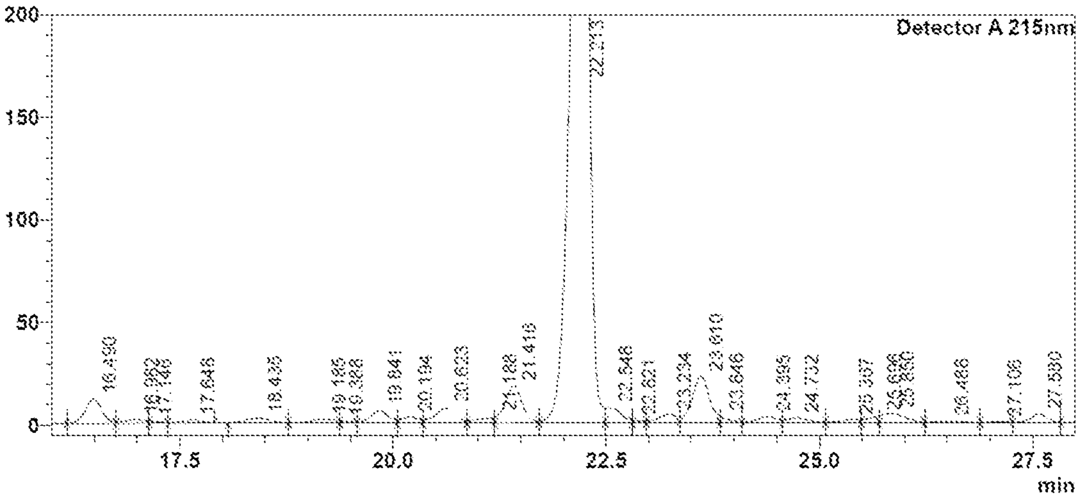
FIG. 2 shows an HPLC chromatogram of a crude peptide of semaglutide prepared in Example 14.

D. 10 g of the fully protected peptide resin obtained in step C was added into 100 mL of the lysis solution with a ratio of TFA:EDT:DMS:thioanisole:Tis:$H_2O$=90:2:2:2:2:2 (volume ratio) at 15° C., and heated up to 30° C., continued to stir and react for 3 h. Then, the reaction mixture was filtered through a sand core funnel, and the filtered resin was washed with 30 mL of TFA. The operation was repeated twice, and the filtrates were combined, then concentrated in vacuo until a volume of the filtrate was 30% of the original volume. Then the concentrated solution was slowly added to 300 mL of the pre-cooled isobutyl ether, and centrifuged after sedimentation overnight for 5 times with 200 mL of isobutyl ether each time, to obtain a white solid powder, which was first dried with nitrogen for 4 h, then dried in a vacuum drying oven for 10 h, and then taken out and weighed to obtain 6.05 g of crude semaglutide. The HPLC chromatogram thereof was shown in FIG. 2, and the HPLC purity was 61.34%.

Example 15 Preparation 2 of Crude Peptide of Semaglutide

A. 15 g of Fmoc-Gly-Wang resin with a degree of substitution of 0.30 mmol/g was poured into a reactor, swollen and mixed with 150 ml of DCM for 15 min, and then drained. 150 ml of piperidine/DMF solution with a volume concentration of 20% was added, mixed for 5 minutes at 20-30° C., and then drained. 100 ml of DMF was added, mixed for 5 minutes, and then drained. 150 ml of piperidine/DMF solution with a volume concentration of 20% was added, mixed for 10 minutes at 20-30° C., and then drained. 150 ml of DMF was added, mixed for 5 minutes, and then drained. The resin was washed repeatedly for 8 times with 150 ml of DMF for 5 minutes each time, and after the seventh washing, the filtrate was tested with a pH test paper, and the result showed that the pH was 6.5-7.0 which was qualified.

B. 5.84 g of Fmoc-Arg(Pbf)-OH, 1.74 g of TBTU, and 0.74 g of HOBT were weighed in turn into a clean 1 L of beaker, and 150 ml of DMF/DCM solution with a volume ratio of 1:1 was added. The beaker was placed in ice water, and the mixture was stirred and dissolved at 0-10° C. with a mechanical stirrer. After the temperature was constant, 0.75 mL of DIEA was added, the temperature was maintained and the solution was stirred and activated for 5 min. The above activated solution was slowly added to a reactor, and mixed for 2 h at 20-25° C. After the reaction was completed, the reaction mixture was drained, and 150 ml of DMF was added thereto, followed by mixing for 5 min and draining. The resin was washed repeatedly for 6 times with 150 ml of DMF for 5 minutes each time. The final test with ninhydrin was negative, that is, a Fmoc-Arg-Gly-Wang resin was obtained.

C. According to the deprotection method of step A and the coupling method of step B described above and based on the sequence of main chain amino acids, the remaining amino acids or peptide fragments were coupled in sequence, namely: coupling of Fmoc-Gly-OH, Fmoc-Arg (Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(AEEA-AEEA-γ-Glu(OtBu)-Octadecanedioic acid mono-tert-butyl ester)-OH obtained in Example 12, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr (tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, and Fmoc-His(Trt)-Aib-Glu (OBzl)-Gly-Thr(tBu)-Phe-OBt obtained in Example 7. Fmoc-Gly-OH, Fmoc-Arg (Pbf)-OH, and Fmoc-Val-OH were coupled by a coupling system of DIC/Cl-HOBt and a DMF solvent. Fmoc-Leu-OH, Fmoc-Trp (Boc)-OH, Fmoc-Ile-OH were coupled by a coupling system of TBTU/HOBt/DIEA and a DCM solvent. Fmoc-Glu(OtBu)-OH was coupled by a coupling system of TBTU/Cl-HOBt/DIEA. Fmoc-Phe-OH was coupled by a coupling system of TBTU/HOAt/DIEA. Fmoc-Ala-OH was coupled by a coupling system of TBTU/DIEA. Fmoc-Ser(tBu)-OH was coupled by a coupling system of PyBop/DIEA. Fmoc-Thr(tBu)-OH was coupled by a coupling system of PyAop/DIEA. Fmoc-Lys(AEEA-AEEA-γ-Glu(OtBu)-Octadecanedioic acid mono-tert-butyl ester)-OH was coupled by a coupling system of COMU/DIEA and a mixed solvent of NMP/DMSO=1:1. The resin was washed for 5 times with 100 ml of dichloromethane each time; then washed twice with 100 ml of methanol each time; and then washed twice with 100 ml of dichloromethane each time; finally washed for 3 times with 100 ml of methanol each time, until the resin was fully dispersed. The resin was dried in a vacuum drying oven at 20-30° C. for 4 h to constant weight (weighed twice continuously, with an error of less than 1%). 32.48 g of peptide resin of semaglutide was obtained.

D. 10 g of the fully protected peptide resin obtained in step C was added into 100 mL of the lysis solution with a ratio of TFA:EDT:DMS:thioanisole:Tis:$H_2O$=90:2:2:2:2:2 (volume ratio) at 15° C., and heated up to 30° C., continued to stir and react for 3 h. Then, the reaction mixture was filtered through a sand core funnel, and the filtered resin was washed with 30 mL of TFA. The operation was repeated twice, and the filtrates were combined, then concentrated in vacuo until a volume of the filtrate was 30% of the original volume. Then the concentrated solution was slowly added to 300 mL of the pre-cooled isobutyl ether, and centrifuged after sedimentation overnight for 5 times with 200 mL of isobutyl ether each time, to obtain a white solid powder, which was first dried with nitrogen for 4 h, then dried in a vacuum drying oven for 10 h, and then taken out and weighed to obtain 5.95 g of crude semaglutide, and the HPLC purity thereof was 68.81%.

Example 16 Preparation 3 of Crude Peptide of Semaglutide

A. 20 g of Fmoc-Gly-Wang resin with a degree of substitution of 0.30 mmol/g was poured into a reactor, swollen and mixed with 200 ml of DCM for 15 min, and then drained. 200 ml of piperidine/DMF solution with a volume concentration of 20% was added, mixed for 5 minutes at 20-30° C., and then drained. 200 ml of DMF was added, mixed for 5 minutes, and then drained. 200 ml of piperidine/DMF solution with a volume concentration of 20% was added, mixed for 10 minutes at 20-30° C., and then drained. 200 ml of DMF was added, mixed for 5 minutes, and then drained. The resin was washed repeatedly for 8 times with 200 ml of DMF for 5 minutes each time, and after the seventh washing, the filtrate was tested with a pH test paper, and the result showed that the pH was 6.5-7.0 which was qualified.

B. 7.78 g of Fmoc-Arg(Pbf)-OH, 2.32 g of TBTU, and 0.98 g of HOBT were weighed in turn into a clean 1 L of beaker, and 200 ml of DMF/DCM solution with a volume ratio of 1:1 was added. The beaker was placed in ice water, and the mixture was stirred and dissolved at 0-10° C. with a mechanical stirrer. After the temperature was constant, 1.00 mL of DIEA was added, the temperature was maintained and the solution was stirred and activated for 5 min. The above activated solution was slowly added to a reactor, and mixed for 2 h at 20-25° C. After the reaction was completed, the reaction mixture was drained, and 200 ml of DMF was added thereto, followed by mixing for 5 min and draining. The resin was washed repeatedly for 6 times with 200 ml of DMF for 5 minutes each time. The final test with ninhydrin was negative, that is, a Fmoc-Arg-Gly-Wang resin was obtained.

C. According to the deprotection method of step A and the coupling method of step B described above and based on the sequence of main chain amino acids, the remaining amino acids or peptide fragments were coupled in sequence, namely: Fmoc-Gly-OH, Fmoc-Arg (Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(AEEA-AEEA-γ-Glu (OtBu)-Octadecanedioic acid mono-tert-butyl ester)-OH obtained in Example 12, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, and Fmoc-His(Trt)-Aib-Glu (OBzl)-Gly-Thr(tBu)-Phe-OH obtained in Example 10. Fmoc-Gly-OH, Fmoc-Arg (Pbf)-OH, and Fmoc-Val-OH were coupled by a coupling system of DIC/Cl-HOBt and a DMF solvent. Fmoc-Leu-OH, Fmoc-Trp (Boc)-OH, Fmoc-Ile-OH were coupled by a coupling system of TBTU/HOBt/DIEA and a DCM solvent. Fmoc-Glu(OtBu)-OH was coupled by a coupling system of TBTU/Cl-HOBt/DIEA. Fmoc-Phe-OH was coupled by a coupling system of TBTU/HOAt/DIEA. Fmoc-Ala-OH was coupled by a coupling system of TBTU/DIEA. Fmoc-Ser(tBu)-OH was coupled by a coupling system of PyBop/DIEA. Fmoc-Thr(tBu)-OH was coupled by a coupling system of PyAop/DIEA. Fmoc-Lys(AEEA-AEEA-γ-Glu(OtBu)-Octadecanedioic acid mono-tert-butyl ester)-OH was coupled by a coupling system of COMU/DIEA and a mixed solvent of NMP/DMSO=1:1. The resin was washed for 5 times with 100 ml of dichloromethane each time; then washed twice with 100 ml of methanol each time; and then washed twice with 100 ml of dichloromethane each time; finally washed for 3 times with 100 ml of methanol each time, until the resin was fully dispersed. The resin was dried in a vacuum drying oven at 20-30° C. for 4 h to constant weight (weighed twice continuously, with an error of less than 1%). 42.18 g of peptide resin of semaglutide was obtained.

D. 10 g of the fully protected peptide resin obtained in step C was added into 100 mL of the lysis solution with a ratio of TFA:EDT:DMS:thioanisole:Tis:$H_2O$=90:2:2:2:2:2 (volume ratio) at 15° C., and heated up to 30° C., continued to stir and react for 3 h. Then, the reaction mixture was filtered through a sand core funnel, and the filtered resin was washed with 30 mL of TFA. The operation was repeated twice, and the filtrates were combined, then concentrated in vacuo until a volume of the filtrate was 30% of the original volume. Then the concentrated solution was slowly added to 300 mL of the pre-cooled isobutyl ether, and centrifuged after sedimentation overnight for 5 times with 200 mL of isobutyl ether each time, to obtain a white solid powder, which was first dried with nitrogen for 4 h, then dried in a vacuum drying oven for 10 h, and then taken out and weighed to obtain 6.12 g of crude semaglutide, and the HPLC purity thereof was 66.24%.

Example 17 Preparation of Refined Peptide of Semaglutide

Figure 3:
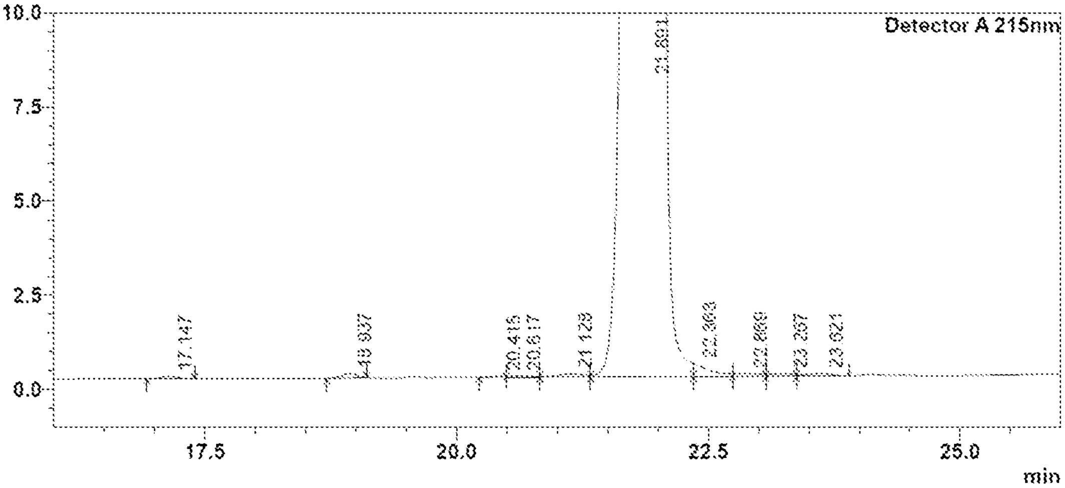
FIG. 3 shows an HPLC chromatogram of a refined peptide of semaglutide prepared in Example 17.

The crude semaglutide obtained in Example 15 was dissolved in dilute ammonia water, the pH of the solution of crude semaglutide was adjusted to 8.0-8.5 with phosphoric acid, followed by filtering to obtain a solution of crude peptide of semaglutide. HPLC linear gradient elution was performed on the solution of crude peptide of semaglutide by using octyl-bonded silica gel as a stationary phase and ammonium chloride and acetonitrile as a mobile phase. The fractions of semaglutide were collected, and part of acetonitrile was removed by rotary evaporation using a rotary evaporator, to obtain a primary purification solution of semaglutide. HPLC linear elution was performed on the primary purification solution of semaglutide by using octyl-bonded silica gel as a stationary phase, and aqueous solution of potassium dihydrogen phosphate having pH adjusted with phosphoric acid, and a mixed solvent of acetonitrile and isopropanol as mobile phase. The fractions of semaglutide were collected, and part of acetonitrile was removed by rotary evaporation using a rotary evaporator, to obtain a secondary purification solution of semaglutide. HPLC linear elution was performed on the secondary purification solution of semaglutide by using octyl-bonded silica gel as a stationary phase and aqueous ammonium bicarbonate solution and acetonitrile as a mobile phase. The fractions of semaglutide were collected, acetonitrile and most of water were removed by rotary evaporation using a rotary evaporator, and lyophilized to obtain 2.86 g of refined peptide of semaglutide. The HPLC purity thereof was 99.8%. The HPLC chromatogram was shown in FIG. 3, and the purification yield was 64.20%.

What is claimed is:

1. A method for preparing semaglutide, comprising: performing a solid-phase synthesis to obtain a semaglutide resin, cleaving and deprotecting the semaglutide resin to obtain a crude peptide of semaglutide, purifying, and lyophilizing to obtain a refined peptide of semaglutide; wherein a monomer $R_1$-His($R_2$)-Aib-Glu($OR_3$)-Gly-Thr($R_4$)-Phe-$R_5$ is used at positions 1-6 and has a formula of:

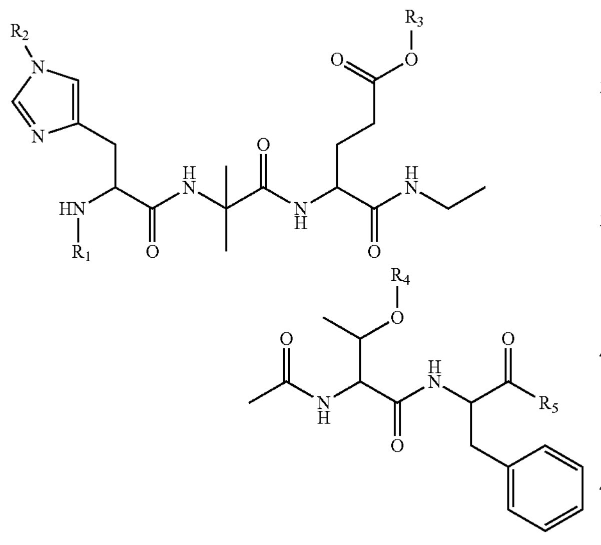

$R_1$ is hydrogen or an amino protecting group,
$R_2$ is hydrogen or an amino protecting group,
$R_3$ is an ester protecting group,
$R_4$ is hydrogen or a hydroxyl protecting group, and
$R_5$ is selected from the group consisting of OH, Cl, OBt, OSu, and OPfp.

2. The method according to claim 1, wherein $R_1$ is selected from the group consisting of Fmoc, Dde, Alloc, Boc, Trt, Dmb, Mmt, and Mtt.

3. The method according to claim 1, wherein $R_2$ is selected from the group consisting of Fmoc, Boc, Trt, Dmb, Mmt, and Mtt.

4. The method according to claim 1, wherein $R_3$ is selected from tBu or Bzl.

5. The method according to claim 1, wherein $R_4$ is selected from tBu or Bzl.

6. The method according to claim 1, wherein $R_5$ is selected from the group consisting of OH, OBt, OSu, and OPfp.

7. The method according to claim 1, wherein $R_1$ is Boc, $R_2$ is Trt, $R_3$ is tBu, $R_4$ is tBu, and $R_5$ is OH.

8. The method according to claim 1, wherein the method further comprises using a monomer Fmoc-Lys(AEEA-AEEA-γ-Glu(OtBu)-Octadecanedioic acid mono-tert-butyl ester)-OH at position 20.

9. The method according to claim 8, wherein a monomer Fmoc-Lys(AEEA-AEEA-γ-Glu(OtBu)-Octadecanedioic acid mono-tert-butyl ester)-OH is used at position 20, and a monomer Boc-His(Trt)-Aib-Glu(OtBu)-Gly-Thr(tBu)-Phe-OH is used at positions 1~6.

10. The method according to claim 1, wherein the $R_1$-His($R_2$)-Aib-Glu($OR_3$)-Gly-Thr($R_4$)-Phe-$R_5$ is coupled by a coupling system of DIC/HOBt.

11. The method according to claim 1, wherein the monomer $R_1$-His($R_2$)-Aib-Glu($OR_3$)-Gly-Thr($R_4$)-Phe-$R_5$ is obtained by coupling $R_1$-His($R_2$)-Aib-OH and a $R_6$-Glu($OR_3$)-Gly-Thr($R_4$)-Phe-resin, wherein $R_6$ is selected from the group consisting of Fmoc, Dde, Alloc, Boc, Trt, Dmb, Mmt, and Mtt.

12. The method according to claim 11, wherein the $R_6$-Glu($OR_3$)-Gly-Thr($R_4$)-Phe-resin is obtained by coupling $R_6$-Glu($OR_3$)-Gly-OH and a $R_7$-Thr($R_4$)-Phe-resin, wherein $R_7$ is selected from the group consisting of Fmoc, Dde, Alloc, Boc, Trt, Dmb, Mmt, and Mtt.

13. The method according to claim 1, wherein the monomer $R_1$-His($R_2$)-Aib-Glu($OR_3$)-Gly-Thr($R_4$)-Phe-$R_5$ is obtained by coupling $R_1$-His($R_2$)-Aib-Glu($OR_3$)-Gly-OH and a $R_7$-Thr($R_4$)-Phe-resin, wherein $R_7$ is selected from the group consisting of Fmoc, Dde, Alloc, Boc, Trt, Dmb, Mmt, and Mtt.

14. The method according to claim 13, wherein $R_1$-His($R_2$)-Aib-Glu($OR_3$)-Gly-OH is obtained by coupling $R_1$-His($R_2$)-Aib-OH and a $R_6$-Glu($OR_3$)-Gly-resin, wherein $R_6$ is selected from the group consisting of Fmoc, Dde, Alloc, Boc, Trt, Dmb, Mmt, and Mtt.

* * * * *